US00PP32325P2

(12) United States Plant Patent
Hansen

(10) Patent No.: US PP32,325 P2
(45) Date of Patent: Oct. 13, 2020

(54) ***PHLOX* PLANT NAMED 'ROCKY ROAD PERIWINKLE'**

(50) Latin Name: ***Phlox* hybrid**
Varietal Denomination: Rocky Road Periwinkle

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,084

(22) Filed: Jan. 30, 2020

(51) Int. Cl.
*A01H 6/70* (2018.01)
*A01H 5/02* (2018.01)

(52) U.S. Cl.
USPC ..... Plt./320

(58) Field of Classification Search
USPC ..... Plt./320
See application file for complete search history.

*Primary Examiner* — Annette H Para

(57) ABSTRACT

A unique cultivar of Hybrid Creeping *Phlox* named 'Rocky Road Periwinkle' characterized by vigorous, dense, spreading, multi-stemmed, winter-hardy habit with short, bright glossy-green, linear leaves. Flowering begins in mid-April and continues up to five weeks, in cool weather, on heavily-branched peduncles and completely cover the plant in peak season. Petals are periwinkle-blue with a small notch and the tips of the petals. The new plant is able to withstand dry conditions once established, and the foliage stays clean and resists mildew. The new plant is especially suitable for the landscape as a potted plant and in the garden as a specimen or en masse.

1 Drawing Sheet

Botanical classification: *Phlox* hybrid.
Variety denomination: 'Rocky Road Periwinkle'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 1, 2019. Subsequently, the new plant was advertised in the "Walters Gardens 19-20 Catalog" by Walters Gardens, Inc. released on May 29, 2019. The claimed plant was first sold on Jul. 8, 2019 by Walters Gardens, Inc., who obtained the plant and all information relating thereto, from the inventor. No plants of *Phlox* 'Rocky Road Periwinkle' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Hybrid Creeping *Phlox*, known as *Phlox* 'Rocky Road Periwinkle' and will be referred to hereafter by its cultivar name, 'Rocky Road Periwinkle', or the "new plant". The new plant was hybridized by the inventor at a wholesale perennial nursery in Zeeland, Mich. on Apr. 30, 2015 as a cross between *Phlox bifida* 'Top Notch' (not patented) as the female or seed parent and *Phlox kelseyi* 'Lemhi Purple' (not patented) as the male or pollen parent. The new plant passed initial evaluation on the spring of 2017 and was assigned the breeder code 15-32-1 through the remaining evaluation process. 'Rocky Road Periwinkle' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Rocky Road Periwinkle' is unique from all other Hybrid Spring *Phlox* known to the inventor. The nearest comparison plants known to the inventor include: the female and male parents, 'Lemhi Purple' (not patented), 'Top Notch', 'Violet Pinwheels' U.S. Plant Pat. No. 25,884, 'Rocky Road Pink' U.S. Plant patent application Ser. No. 16/350,917, 'Rocky Road Magenta' U.S. Plant patent application Ser. No. 16/350,916, 'Rocky Road Violet Blue' copending U.S. Plant patent application Ser. No. 16/873,083, 'Rocky Road Grape' copending U.S. Plant patent application Ser. NO. 16/873,085, and 'Plumtastic' U.S. Plant Pat. No. 28,896. 'Top Notch' has a taller habit, the flowers are more deeply notched at the petal apex, the soft blue petals are narrower and finely textured. 'Lemhi Purple' has a slightly shorter habit and deeper purple-violet flowers without a notched petal apex. 'Violet Pinwheels' has flowers that are more violet-blue and the petals are more deeply cleft at the apices. 'Rocky Road Pink' has pastel rosy-pink flowers with a dark pink eye. 'Rocky Road Magenta' has magenta purple flowers without a notched petal apex and the flowers are much larger. 'Rocky Road Violet Blue' has violet blue flowers. 'Rocky Road Grape' has a slightly taller habit and the flowers are reddish-purple. 'Plumtastic' has flowers of violet-pink with purple markings near the eye, and the flower initially has a light, near-white center that darkens to the same violet-pink at maturity.

*Phlox* 'Rocky Road Periwinkle' differs from and all other *Phlox* known to the inventor in the following repeatedly observed traits in combination:

1. Vigorous plants of dense spreading habit, spreading by rooting stems, producing short, clean, puberulent, bright-green, linear leaves;
2. Multiple heavily-branched stems produce branched panicles;
3. Flower beginning in mid-April and continuing up to five weeks, in cooler conditions, completely covering plant at peak flowering;
4. Flowers of periwinkle-blue with small notches at the tip of the petals;
5. Plant is able to withstand dry conditions once established.

BRIEF DESCRIPTION OF THE DRAWINGS

The photographs of the new plant demonstrate the unique traits of *Phlox* 'Rocky Road Periwinkle' and the overall appearance of the plant at three-years-old growing in a full-sun trial beds in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
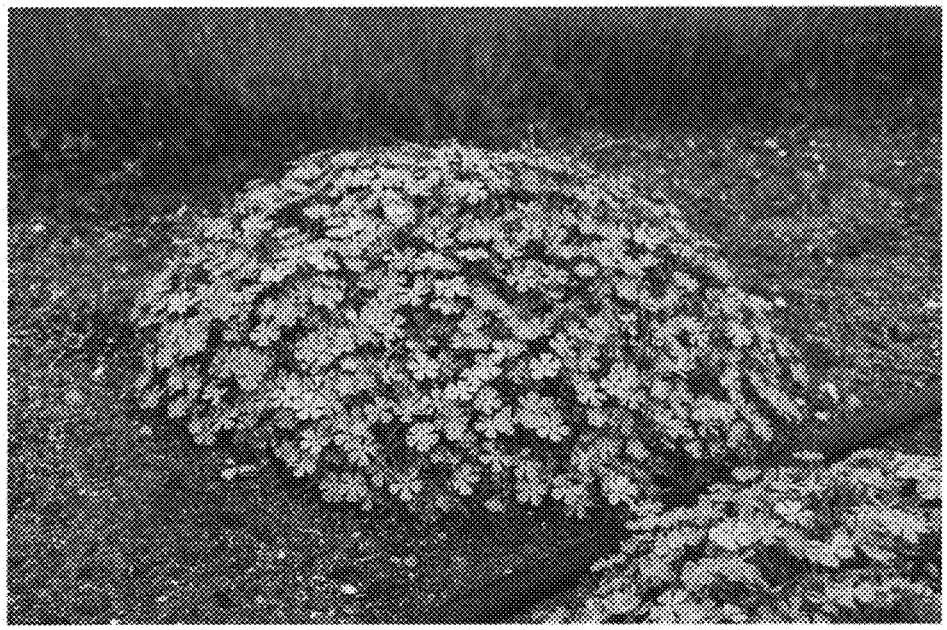
FIG. 1 shows a landscape habit view of the new plant in peak flower.
Figure 2:
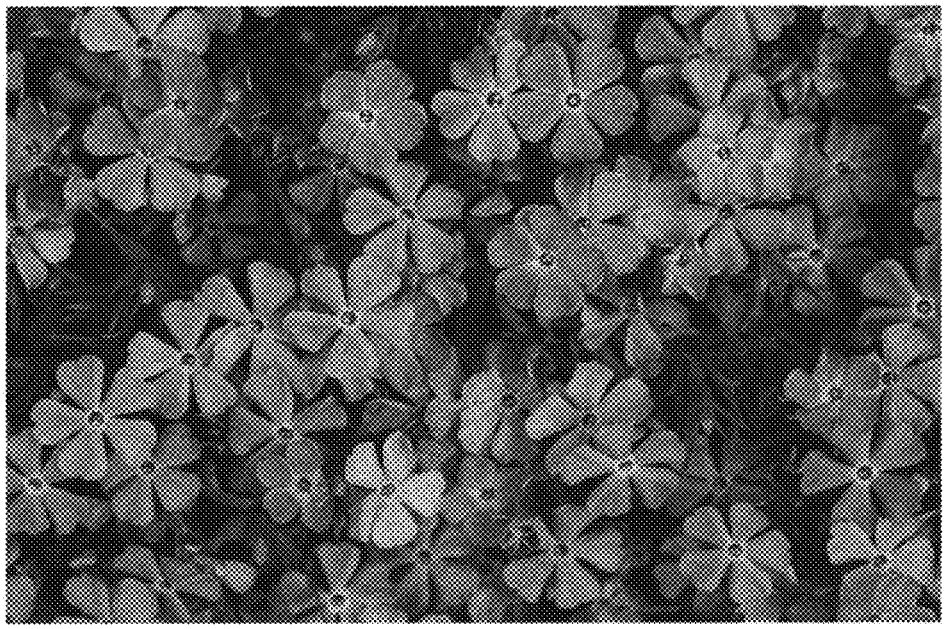
FIG. 2 shows a close-up of the flowers and buds.

The following descriptions and color references are based on the 2015 edition of The Royal Horticultural Society Colour Chart except where common dictionary terms are used. *Phlox* 'Rocky Road Periwinkle' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full-sun trial garden of a wholesale perennial nursery in Zeeland, Mich. with supplemental fertilizer and water as needed.

Botanical classification: *Phlox* hybrid;

Parentage: Female or seed parent is *Phlox bifida* 'Top Notch', male or pollen parent is *Phlox kelseyi* 'Lemhi Purple';

Plant habit: Winter-hardy, evergreen herbaceous perennial; short, dense, producing about 60 to 80 stiff, highly-branched prostrate stems; foliage 8.0 cm tall and 48.0 cm wide, average 7.0 cm tall and 44.0 cm wide; flowering to 10.0 cm tall and 50.0 cm wide;

Propagation: Stem cuttings; rooting in about 3 weeks;

Time to produce finished crop in 3.8 liter pots: About 8 to 12 weeks; moderately vigorous;

Root: Fibrous and freely branching; color creamy white to tan depending on soil type;

Leaves: Simple; opposite proximally, whorled distally; linear to subulate; apex narrowly acute to mucronulate; base truncate, clasping; margin entire, ciliolate; puberulent both adaxial and abaxial; about 24.0 mm long by about 3.0 mm wide, average about 19.5 mm long and 2.5 mm wide;

Leaf color: Adaxial expanding and mature nearest RHS 138A; abaxial expanding and mature between RHS 138A and RHS 146D;

Foliage fragrance: None detected;

Veins: Pinnate; not conspicuous adaxial and abaxial;

Vein color: Same color as surround leaf;

Petiole: Leaves sessile;

Stems: Cylindrical; flexible; wiry; prostrate; highly branching; to about 6.0 mm long and 1.0 mm diameter near base;

Stem color: Color nearest RHS 145A when exposed;

Nodes: Proximally about 5.0 mm apart; distally less than 1.0 mm apart;

Node color: Color nearest RHS 183D;

Inflorescence: Upright to outwardly; about 2.5 cm long and 4.0 cm wide; average of 3 flowers;

Flowers: Perfect; salverform; mostly flat faced; about 20.0 mm across face and 15.0 mm long; with fused corolla tube about 11.5 mm long and 2.5 mm diameter near face; attitude upright to outwardly;

Flower longevity: About 5 days on plant; self-cleaning;

Flower fragrance: Not detected;

Buds one to two days prior to opening: Narrowly oblanceolate, to narrowly clavate; bluntly acute apex with rounded base; petals implicate; about 17.0 mm long, 7.0 mm long in terminal bulb portion and 10.0 mm long in tube; corolla tube to 2.5 mm diameter, bulb to 4.0 mm diameter;

Bud color: Exposed petal bulb portion nearest RHS N88C, between tube and bulb nearest RHS 144A, corolla tube basal 1.0 mm nearest RHS 145B and distal tube between RHS157B and RHS 76C; calyx between RHS 138B and RHS 138A with strong blush in high light exposure of nearest RHS 187A;

Petals: Five; consisting of limb and claw base fused into corolla tube; apex rounded and sharply and shallowly cleft to about 1.0 mm deep; limbs not imbricate; margin entire; glabrous adaxial and abaxial;

Petal size: Limb about 9.0 mm long and 8.0 mm wide near middle; tube about 11.5 mm long and 2.5 mm diameter;

Petal color upon opening:

*Adaxial*.—Limb nearest RHS N87C without marks near center eye; proximal 4.0 mm of tube transitioning from nearest RHS 145C to nearest RHS 145D at base, remaining distal tube portion nearest RHS 85D.

*Abaxial*.—Limb nearest RHS N87D, proximal 1.0 mm of tube nearest RHS 145C, next proximal 3.0 mm nearest RHS 145D, remaining distal tube portion nearest RHS 85D.

Petal color upon maturity:

*Adaxial*.—Limb between RHS N87C and RHS N87D, without marks near center eye; proximal 4.0 mm of tube transitioning from nearest RHS 145C to nearest RHS 145D at base, remaining distal tube portion nearest RHS 85D.

*Abaxial*.—Limb nearest RHS N87D, proximal 1.0 mm of tube nearest RHS 145C, next proximal 3.0 mm nearest RHS 145D, remaining distal tube portion nearest RHS 85D.

*Androecium*.—Typically five.

Filaments: Typically five, adnate to inner corolla to various heights about 7.0 mm to 10.0 mm from base; free in the distal 1.0 mm to 2.0 mm long and 0.2 mm in diameter; color nearest RHS NN155D;

Anther: Five; oblong elliptic; basifixed; oblong, about 1.5 mm long by 0.7 mm wide; color nearest RHS 21B;

Pollen: Nearly microscopic; color between RHS 25A and RHS N25C;

Gynoecium: One pistil per flower; 12.0 mm long;

Style: Cylindrical; about 8.5 mm long and 0.3 mm diameter when flower is mature; persistent after flower abscission; color nearest RHS 150D;

Stigma: Trifid in proximal 1.5 mm long, about 0.3 mm diameter; color nearest RHS 8A;

Ovary: Inferior; ellipsoidal; glabrous; acute apex and truncate base; about 1.5 mm long and 1.0 mm diameter; color nearest RHS 144A;

Calyx: Campanulate; pubescent abaxial, glabrous adaxial; about 10.0 mm long and 3.5 mm across at apex;

Sepals: Five; lanceolate; glabrous adaxial and pubescent to puberulent abaxial; narrowly acute apex, fused in basal 4.0 mm; margin entire; matte abaxial, and lustrous adaxial; individually about 10.0 mm long and 1.0 mm wide at fusion;

Sepal color: Adaxial nearest RHS 138A; abaxial between RHS 138B and RHS 138A with strong blush in high light exposure of nearest RHS 187A;

Peduncle: Finely puberulent; strong, flexible; mostly upright; cylindrical; about 1.5 mm diameter at base and 1.5 cm long;

Peduncle color: Low light or ventrally nearest RHS 146D; high light or ventrally nearest RHS 146C with strong blush to solid RHS 187A;

Pedicle: Cylindrical; glabrous; flexible; upright to outwardly; variable lengths from about 3.0 mm to 6.0 mm long and 0.7 mm diameter;

Pedicle color: Variable depending on light exposure; low light or ventrally nearest RHS 145A; high light or dorsally nearest RHS 146C with strong blush to solid RHS 187A;

Fruit and seeds: Not observed;

Hardiness and culture: The new plant grows best with full sun, light moisture and deep drainage; hardy to at least from USDA zone 4 through 8.

Disease and pest resistance: *Phlox* 'Rocky Road Periwinkle' demonstrates excellent powdery mildew resistance under conditions that would normally show symptoms.

I claim:

1. A new and distinct cultivar of Hybrid Creeping *Phlox, Phlox* plant named 'Rocky Road Periwinkle' as herein described and illustrated.

* * * * *